(12) United States Patent
Shadforth et al.

(10) Patent No.: US 8,688,386 B2
(45) Date of Patent: Apr. 1, 2014

(54) ANALYTE TESTING METHOD AND DEVICE FOR CALCULATING BASAL INSULIN THERAPY

(75) Inventors: Ian Shadforth, San Francisco, CA (US); David Price, Pleasanton, CA (US); Zara Sieh, Pleasanton, CA (US); Brenda Montgomery, Bellevue, WA (US); Eric David Bergman, Menlo Park, CA (US)

(73) Assignee: LifeScan, Inc., Milpitas, CA (US)

( * ) Notice: Subject to any disclaimer, the term of this patent is extended or adjusted under 35 U.S.C. 154(b) by 410 days.

(21) Appl. No.: 12/826,670

(22) Filed: Jun. 30, 2010

(65) Prior Publication Data

US 2010/0332142 A1 Dec. 30, 2010

Related U.S. Application Data

(60) Provisional application No. 61/222,006, filed on Jun. 30, 2009.

(51) Int. Cl.
- *G01N 33/48* (2006.01)
- *G01N 31/00* (2006.01)
- *G06G 7/48* (2006.01)
- *G06G 7/58* (2006.01)

(52) U.S. Cl.
USPC ............ 702/19; 702/22; 703/11; 703/12

(58) Field of Classification Search
None
See application file for complete search history.

(56) References Cited

U.S. PATENT DOCUMENTS

| | | | |
|---|---|---|---|
| 4,731,726 | A  | 3/1988  | Allen |
| 5,251,126 | A  | 10/1993 | Kahn et al. |
| 5,822,715 | A  | 10/1998 | Worthington et al. |
| 6,179,979 | B1 | 1/2001  | Hodges et al. |
| 6,193,873 | B1 | 2/2001  | Ohara et al. |
| 6,280,409 | B1 | 8/2001  | Stone et al. |
| 6,284,125 | B1 | 9/2001  | Hodges et al. |
| 6,309,884 | B1 | 10/2001 | Cooper et al. |
| 6,379,301 | B1 | 4/2002  | Worthington et al. |
| 6,413,410 | B1 | 7/2002  | Hodges et al. |
| 6,425,863 | B1 | 7/2002  | Werner et al. |
| 6,475,372 | B1 | 11/2002 | Ohara et al. |
| 6,544,212 | B2 | 4/2003  | Galley et al. |
| 6,558,351 | B1 | 5/2003  | Steil et al. |
| 6,572,542 | B1 | 6/2003  | Houben et al. |
| 6,633,772 | B2 | 10/2003 | Ford et al. |
| 6,635,167 | B1 | 10/2003 | Batman et al. |
| 6,656,114 | B1 | 12/2003 | Poulsen et al. |

(Continued)

FOREIGN PATENT DOCUMENTS

| | | |
|---|---|---|
| EP | 0483595 B1 | 12/2001 |
| EP | 1338295 A1 | 8/2003 |

(Continued)

OTHER PUBLICATIONS

International PCT Patent Application No. PCT/US2010/040434, International Search Report, dated Oct. 20, 2010, 3 pgs, European Patent Office, Rijswijk.

(Continued)

*Primary Examiner* — Larry D Riggs, II

(57) ABSTRACT

Described herein are various methods to ensure safety and the compliance of therapeutic diabetes protocols. The method can be achieved by performing safeguards against hypoglycemia of the user prior to any change in basal insulin dosage based on the plurality of data.

27 Claims, 11 Drawing Sheets

(56) References Cited

U.S. PATENT DOCUMENTS

| | | |
|---|---|---|
| 6,691,043 B2 | 2/2004 | Ribeiro, Jr. et al. |
| 6,716,577 B1 | 4/2004 | Yu et al. |
| 6,749,887 B1 | 6/2004 | Dick et al. |
| 6,862,466 B2 | 3/2005 | Ackerman |
| 6,863,801 B2 | 3/2005 | Hodges et al. |
| 6,890,421 B2 | 5/2005 | Ohara et al. |
| 6,941,163 B2 | 9/2005 | Ford et al. |
| 7,022,072 B2 | 4/2006 | Fox et al. |
| 7,024,236 B2 | 4/2006 | Ford et al. |
| 7,045,046 B2 | 5/2006 | Chambers et al. |
| 7,060,059 B2 | 6/2006 | Keith et al. |
| 7,179,226 B2 | 2/2007 | Crothall et al. |
| 7,204,823 B2 | 4/2007 | Estes et al. |
| 7,241,265 B2 | 7/2007 | Cummings et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,291,256 B2 | 11/2007 | Teodorczyk et al. |
| 7,354,420 B2 | 4/2008 | Steil et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,498,132 B2 | 3/2009 | Yu et al. |
| 7,509,156 B2 | 3/2009 | Flanders |
| 7,553,281 B2 | 6/2009 | Hellwig et al. |
| 7,651,489 B2 | 1/2010 | Estes et al. |
| 2002/0019707 A1 | 2/2002 | Cohen et al. |
| 2002/0026111 A1 | 2/2002 | Ackerman |
| 2003/0108976 A1 | 6/2003 | Braig et al. |
| 2003/0175806 A1 | 9/2003 | Rule et al. |
| 2003/0208113 A1 | 11/2003 | Mault et al. |
| 2003/0211617 A1 | 11/2003 | Jones |
| 2003/0220814 A1 | 11/2003 | Gordon |
| 2004/0059201 A1 | 3/2004 | Ginsberg |
| 2005/0004439 A1 | 1/2005 | Shin et al. |
| 2005/0027182 A1 | 2/2005 | Siddiqui et al. |
| 2005/0090726 A1 | 4/2005 | Ackerman |
| 2005/0096511 A1 | 5/2005 | Fox et al. |
| 2005/0096512 A1 | 5/2005 | Fox et al. |
| 2005/0113653 A1 | 5/2005 | Fox et al. |
| 2005/0143864 A1 | 6/2005 | Bloomquist |
| 2005/0176153 A1 | 8/2005 | O'Hara et al. |
| 2005/0182358 A1 | 8/2005 | Veit et al. |
| 2005/0214892 A1 | 9/2005 | Kovatchev et al. |
| 2007/0010950 A1 | 1/2007 | Abensour et al. |
| 2007/0016127 A1 | 1/2007 | Staib et al. |
| 2007/0016449 A1 | 1/2007 | Cohen et al. |
| 2007/0060803 A1 | 3/2007 | Liljeryd et al. |
| 2007/0060813 A1 | 3/2007 | Chang |
| 2007/0083335 A1 | 4/2007 | Moerman et al. |
| 2007/0118589 A1 | 5/2007 | Brown |
| 2007/0173761 A1 | 7/2007 | Kanderiab, Jr. et al. |
| 2007/0208246 A1 | 9/2007 | Brauker et al. |
| 2007/0231914 A1 | 10/2007 | Deng et al. |
| 2007/0232880 A1 | 10/2007 | Siddiqui et al. |
| 2007/0287985 A1 | 12/2007 | Estes et al. |
| 2008/0045819 A1 | 2/2008 | Emoto et al. |
| 2008/0045825 A1 | 2/2008 | Melker et al. |
| 2008/0052057 A1 | 2/2008 | Brown |
| 2008/0097289 A1 | 4/2008 | Steil et al. |
| 2008/0119702 A1 | 5/2008 | Reggiardo et al. |
| 2008/0119710 A1 | 5/2008 | Reggiardo et al. |
| 2008/0125636 A1 | 5/2008 | Ward et al. |
| 2008/0139910 A1 | 6/2008 | Mastrototaro et al. |
| 2008/0154513 A1 | 6/2008 | Kovatchev et al. |
| 2008/0171967 A1 | 7/2008 | Bloomquist |
| 2008/0172027 A1 | 7/2008 | Bloomquist |
| 2008/0172028 A1 | 7/2008 | Bloomquist |
| 2008/0172029 A1 | 7/2008 | Bloomquist |
| 2008/0172031 A1 | 7/2008 | Bloomquist |
| 2008/0177154 A1 | 7/2008 | Hansen et al. |
| 2008/0183060 A1 | 7/2008 | Steil et al. |
| 2008/0187943 A1 | 8/2008 | Buse et al. |
| 2008/0188796 A1 | 8/2008 | Steil et al. |
| 2008/0199465 A1 | 8/2008 | Lake et al. |
| 2008/0206799 A1 | 8/2008 | Blomquist |
| 2008/0234992 A1* | 9/2008 | Ray et al. ........................ 703/2 |
| 2008/0235053 A1 | 9/2008 | Ray et al. |
| 2008/0255438 A1 | 10/2008 | Saidara et al. |
| 2008/0262088 A1 | 10/2008 | Hauck et al. |
| 2008/0268485 A1 | 10/2008 | Guarino et al. |
| 2008/0269585 A1 | 10/2008 | Ginsberg |
| 2008/0294024 A1 | 11/2008 | Cosentino et al. |
| 2008/0312512 A1 | 12/2008 | Brukalo et al. |
| 2008/0312518 A1 | 12/2008 | Jina et al. |
| 2009/0006129 A1 | 1/2009 | Thukral et al. |
| 2009/0018495 A1 | 1/2009 | Panduro |
| 2009/0018779 A1 | 1/2009 | Cohen et al. |
| 2009/0030733 A1 | 1/2009 | Cohen et al. |
| 2009/0098587 A1 | 4/2009 | Hetzel et al. |
| 2009/0099506 A1 | 4/2009 | Estes et al. |
| 2009/0099509 A1 | 4/2009 | Estes et al. |
| 2009/0105570 A1 | 4/2009 | Sloan et al. |
| 2009/0112069 A1 | 4/2009 | Kanamori et al. |
| 2009/0112626 A1 | 4/2009 | Talbot et al. |
| 2009/0137455 A1 | 5/2009 | Steiner et al. |
| 2009/0149717 A1 | 6/2009 | Brauer et al. |
| 2009/0150186 A1 | 6/2009 | Cohen et al. |
| 2009/0156923 A1 | 6/2009 | Power et al. |
| 2009/0156924 A1 | 6/2009 | Shariati et al. |
| 2009/0177147 A1 | 7/2009 | Blomquist et al. |
| 2009/0184004 A1 | 7/2009 | Chatiler et al. |
| 2009/0237262 A1 | 9/2009 | Smith et al. |
| 2009/0240127 A1 | 9/2009 | Ray |
| 2009/0247982 A1 | 10/2009 | Krulevitch et al. |
| 2009/0292190 A1 | 11/2009 | Miyashita |
| 2010/0016700 A1 | 1/2010 | Sieh et al. |
| 2010/0041084 A1 | 2/2010 | Stephens et al. |
| 2010/0041960 A1 | 2/2010 | Yuan et al. |
| 2010/0174228 A1 | 7/2010 | Buckingham et al. |

FOREIGN PATENT DOCUMENTS

| | | | |
|---|---|---|---|
| EP | | 1568310 A1 | 8/2005 |
| EP | | 1677226 A1 | 7/2006 |
| EP | | 1770396 A2 | 4/2007 |
| EP | | 1840219 A1 | 10/2007 |
| WO | WO 98/37805 A1 | | 9/1998 |
| WO | WO 02/00112 A2 | | 1/2002 |
| WO | WO 03/030731 A2 | | 4/2003 |
| WO | WO 03/045233 A1 | | 6/2003 |
| WO | WO 2004/015539 A2 | | 2/2004 |
| WO | WO 2004/023972 A2 | | 3/2004 |
| WO | WO 2005/093629 A2 | | 10/2005 |
| WO | WO 2006/066038 A3 | | 6/2006 |
| WO | WO 2006/066583 A1 | | 6/2006 |
| WO | WO 2006/133348 A2 | | 12/2006 |
| WO | WO 2007/005170 A2 | | 1/2007 |
| WO | WO 2007/019289 A1 | | 2/2007 |
| WO | WO 2007/019384 A1 | | 2/2007 |
| WO | WO 2007/028271 A3 | | 3/2007 |
| WO | WO 2007/101260 A2 | | 9/2007 |
| WO | WO 2007/149533 A1 | | 12/2007 |
| WO | WO 2008/071218 A1 | | 6/2008 |
| WO | WO 2008/071444 A1 | | 6/2008 |
| WO | WO 2008/073609 A2 | | 6/2008 |
| WO | WO 2008/094249 A1 | | 8/2008 |
| WO | WO 2009/005952 A3 | | 1/2009 |
| WO | WO 2009/005960 A3 | | 1/2009 |
| WO | WO 2009/016050 A1 | | 2/2009 |
| WO | WO 2009/137661 | | 11/2009 |

OTHER PUBLICATIONS

International Search Report, PCT Application No. PCT/US2010/040383, dated Nov. 4, 2010, 3 pages, European Patent Office, Rijswijk.

International Search Report, PCT Application No. PCT/US2010/040425, Dated Dec. 23, 2010, 7 pages, European Patent Office, Rijswijk, Netherlands.

(56) References Cited

OTHER PUBLICATIONS

Partial International Search Report, Annex to Form PCT/ISA/206, PCT Application No. PCT/US2010/040309, Dated Nov. 29, 2010, 2 pages, European Patent Office, Rijswijk, Netherlands.
International Search Report, PCT Application No. PCT/GB2010/001683, Dated Dec. 22, 2010, 4 pages, European Patent Office, Rijswijk, Netherlands.
Nathan, D.M., *Management of Hyperglycemia in Type 2 Diabetes: A Consensus Algorithm for the Initiation and Adjustment of Therapy*, Diabetes Care, vol. 29 No. 8, 1963-1972, Aug. 2006.
William H. et al. *Numerical Recipes in C: The Art of Scientific Computing*. Cambridge: Cambridge University Press, 1992. ISBN 0-521-43108-5, pp. 226-230.
"Accu-Chek Complete Owner's Booklet", Roche Diagnostics, 2004, XP002636883, Retrieved from internet: URL:https://www.accu-chek.com/us/customer-care/downloads.html [retrieved May 12, 2011], p. 8, pp. 33-40, pp. 46 and 86.
International Search Report, PCT Application No. PCT/US2010/040443, dated May 17, 2011, 3 pages, European Patent Office, Rijswijk, NL.

* cited by examiner

US 8,688,386 B2

ANALYTE TESTING METHOD AND DEVICE FOR CALCULATING BASAL INSULIN THERAPY

This application claims the benefits of priority under 35 USC §119 and/or §120 from prior filed U.S. Provisional Application Ser. No. 61/222,006 filed on Jun. 30, 2009, which applications are incorporated by reference in their entirety into this application.

BACKGROUND

Introduction and management of insulin therapy to a patient with diabetes can be overwhelming to the patient and a burden to the provider due to the complexity of conventional methods and devices for doing so. Significant training of the patient may be necessary. The patient may need to learn, for example, various concepts and actions including hypoglycemia management, injections and the proper use of insulin administration devices, as well as the mechanical, electronic, and software aspects of using a blood glucose meter. In addition, the patient must learn to follow the doctor's instructions in starting and adjusting insulin dosages on a regular basis (e.g., per meal, daily, 2× weekly, or weekly basis).

Detailed instructions as to the prescribed blood glucose testing and insulin titration protocol are typically written out by the health care professional and checked off on a piece of paper. Patients often keep handwritten logs in order to comply. It is not uncommon for a patient to have poor glycemic control even after getting onto insulin therapy. The user can have difficulty determining how much insulin to take before going to bed based on current and previous glucose measurements.

SUMMARY OF THE DISCLOSURE

Applicants have recognized that there is a need for safeguards in self-administered insulin therapy. In providing a solution that is believed to satisfy this need, applicants have provided for a method for management of diabetes of a user with a handheld glucose-insulin data management unit. The data management unit has an analyte test sensor, a processor coupled to a memory and display. The method can be achieved by: measuring a plurality of blood glucose concentration value of the user with the analyte test sensor over a plurality of time periods; collecting data representative of the plurality of fasting blood glucose concentration value with the handheld glucose-insulin data management unit; ascertaining from the collected data whether the user has conducted a minimum number fasting blood glucose concentration measurements within at least one of four prescribed time periods; determining whether the collected data indicate one of a first low blood glucose concentration pattern and a second low blood glucose concentration pattern lower than the first low blood glucose concentration pattern; and upon determination of at least one of the first and second low blood glucose concentration patterns of the user, displaying safety notifications on the display screen of the handheld glucose-insulin data management unit.

In a further embodiment, a method to safeguard basal insulin dose changes with a handheld glucose-insulin data management unit is provided. The data management unit has a test sensor, a processor coupled to a memory and display. The method can be achieved by: collecting data representative of a plurality of fasting blood glucose concentration values as measured by the test sensor of the handheld glucose-insulin data management unit; performing safeguards against hypoglycemia of the user prior to any change in basal insulin dosage based on the plurality of data; and upon completion of the safeguard, recommending one of no change in the current basal insulin dose, an increase or decrease in the current basal insulin dose as a function of at least three consecutive fasting glucose concentration values from the plurality of fasting blood glucose concentration values.

These and other embodiments, features and advantages will become apparent to those skilled in the art when taken with reference to the following more detailed description of the embodiments of the invention in conjunction with the accompanying drawings that are first briefly described here below.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Embodiments described and illustrated herein provide an analyte (e.g., blood glucose) measurement and management device and associated methods that simplify training and guide a patient regarding how to adjust basal insulin therapy. Such methods also notify a user when there is a potential problem and when to contact a doctor. Embodiments of the analyte measurement and management device and system are also beneficial to care providers (for example, physicians) by gathering, organizing and storing information that provides insight into how effective a patient is in following a prescribed analyte management regimen.

In one embodiment, a health care provider ("HCP") may prescribe that a patient take a basal insulin dose on a recurring basis (e.g., before bedtime every day). Basal insulin can refer to background insulin needed to account for regular and continuous glucose metabolism. Typically, a basal insulin dose refers to the injection of a long lasting or intermediate lasting insulin type. If the patient's glucose concentration value is hypo or hyperglycemic, the HCP can recommend that the basal insulin dose be decreased or increased. However, applicant believes that the method for determining exactly how much to increase or decrease a basal insulin dose for a particular time can be difficult to convey to a lay user. To further compound this issue, a user who mistakenly increases an insulin dose by too much can cause serious physiological harm. Determining whether to increase or decrease an insulin basal dose can be based on a sufficient number of fasting glucose concentration values that are hypoglycemic or hyperglycemic. Further, the amount of the increment or decrement can be based on the magnitude of the hypoglycemic or hyperglycemic measurements.

Figure 1:
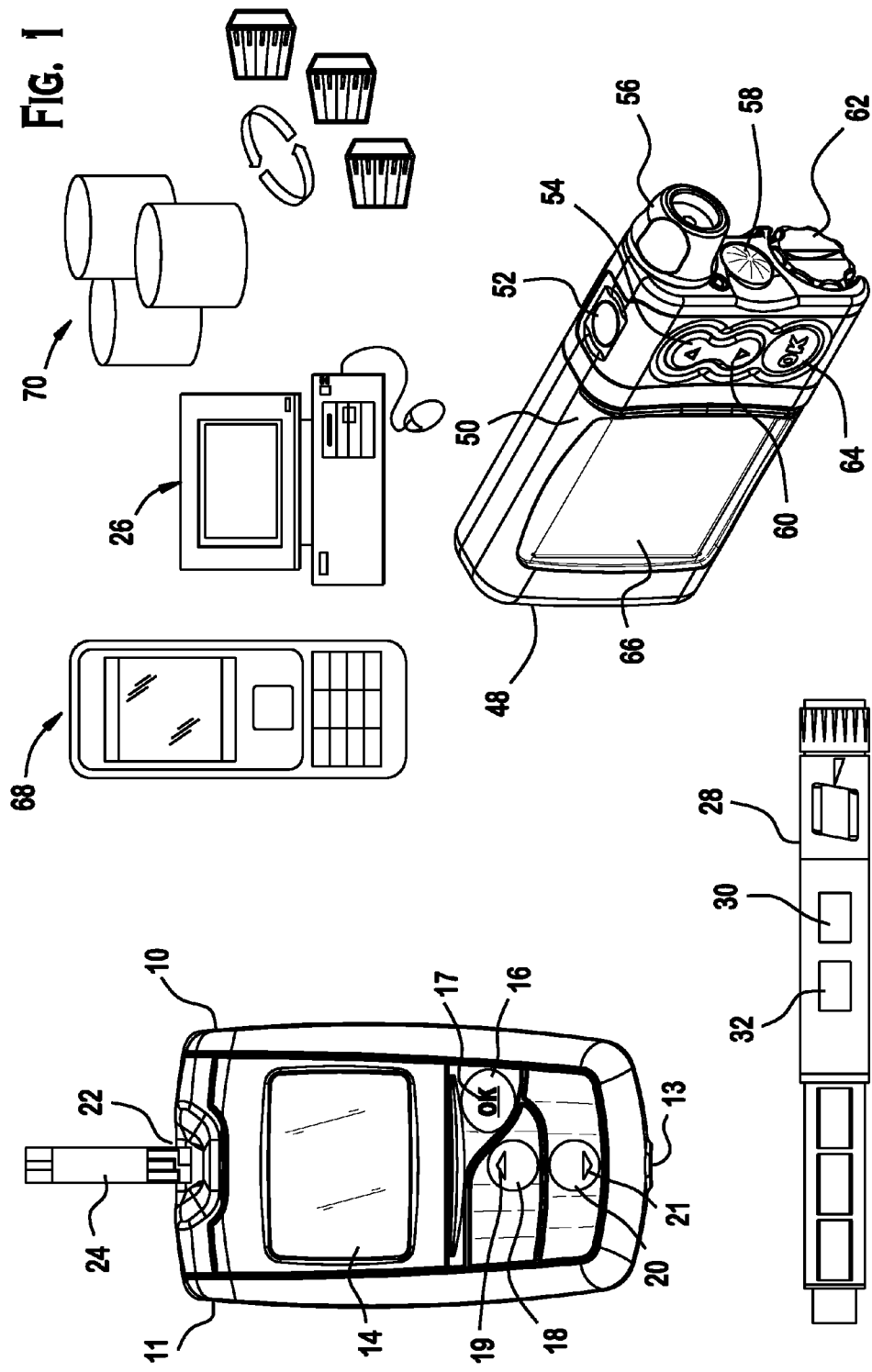
FIG. 1 illustrates a diabetes management system that includes an analyte measurement and management device, therapeutic dosing devices, and data/communication devices, according to an exemplary embodiment described and illustrated herein.

FIG. 1 illustrates a diabetes management system that includes an analyte measurement and management device 10, therapeutic dosing devices (28 and 48), and data/communication devices (68, 26, and 70). Analyte measurement and management device 10 can be configured to wirelessly communicate with a handheld glucose-insulin data management unit or DMU such as, for example, an insulin pen 28, an insulin pump 48, a mobile phone 68 or through a combination of the exemplary handheld glucose-insulin data management unit devices in communication with a personal computer 26 or network server 70, as described herein. As used herein, the nomenclature "DMU" represents either individual unit 10, 28, 48, 68, separately or all of the handheld glucose-insulin data management units (28, 48, 68) usable together in a disease management system. Further, the analyte measurement and management device or DMU 10 is intended to include a glucose meter, a meter, an analyte measurement device, an insulin delivery device or a combination of or an analyte testing and drug delivery device.

DMU 10 can include a housing 11, user interface buttons (16, 18, and 20), a display 14, a strip port 22, and a data port 13, as illustrated in FIG. 1. User interface buttons (16, 18, and 20) can be configured to allow the entry of data, navigation of menus, and execution of commands. Specifically, user interface buttons (16, 18, and 20) include a first user interface button 16, a second user interface button 18, and a third user interface button 20. User interface buttons (16, 18, and 20) include a first marking 17, a second marking 19, and a third marking 21, respectively, which allow a user to navigate through the user interface. Data entered can include values representative of analyte concentration, or in the context of the analyte concentration values coupled with information, which are related to the everyday lifestyle of an individual. Information, which is related to the everyday lifestyle, can include food intake, medication use, occurrence of health check-ups, and general health condition and exercise levels of an individual coupled to or "tagged" with the analyte concentration value of the user at specific time of the day or week.

Figure 2:
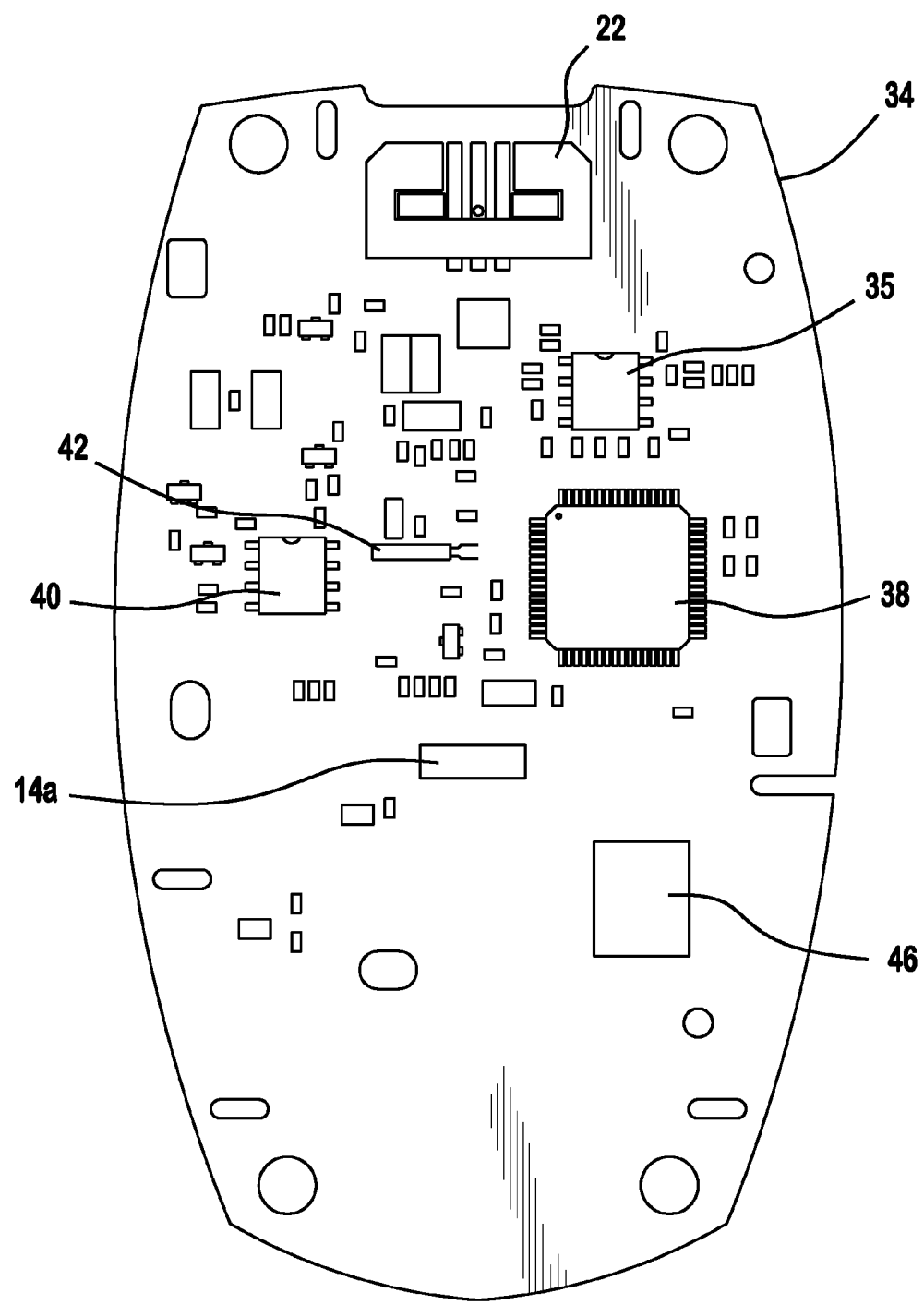
FIG. 2 illustrates a top portion of a circuit board of the analyte measurement and management device, according to an exemplary embodiment described and illustrated herein.
Figure 3:
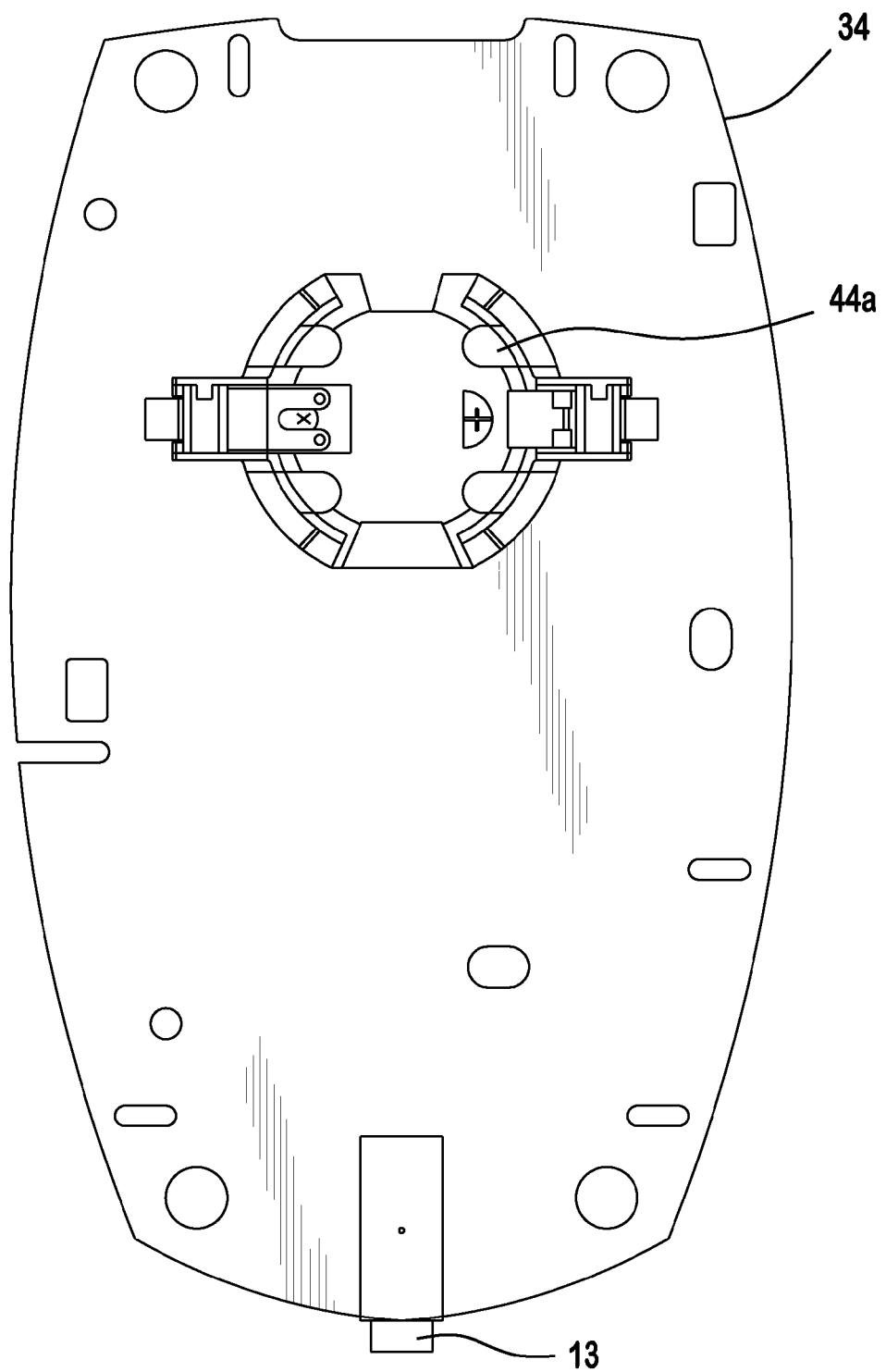
FIG. 3 illustrates a bottom portion of the circuit board of the analyte measurement and management device, according to an exemplary embodiment described and illustrated herein.

The electronic components of DMU 10 can be disposed on a circuit board 34 that is within housing 11. FIGS. 2 and 3 illustrate the electronic components disposed on a top surface and a bottom surface of circuit board 34, respectively. On the top surface, the electronic components include a strip port 22 configured to receive a test strip connector portion of test strip 24, an operational amplifier circuit 35, a microcontroller 38, a display connector 14a, a non-volatile memory 40, a clock 42, and a first wireless module 46. On the bottom surface, the electronic components include a battery connector 44a and a data port 13. Microcontroller 38 can be electrically connected to strip port 22, operational amplifier circuit 35, first wireless module 46, display 14, non-volatile memory 40, clock 42, battery connector 344a, data port 13, and user interface buttons (16, 18, and 20).

Operational amplifier circuit 35 can be two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 38 can be in the form of a mixed signal microprocessor (MSP) such as, for example, the Texas Instrument MSP 430. The MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit (ASIC).

Strip port 22 can be configured to form an electrical connection to the test strip. Display connector 14a can be configured to attach to display 14. Display 14 can be in the form of a liquid crystal display for reporting measured glucose levels, and for facilitating entry of lifestyle related information and for manipulation of graphical data, pictorial results and motion video. Display 14 can optionally include a backlight. Data port 13 can accept a suitable connector attached to a connecting lead, thereby allowing DMU 10 to be linked to an external device such as a personal computer. Data port 13 can be any port that allows for transmission of data such as, for example, a serial, USB, or a parallel port. Clock 42 can be configured for measuring time and be in the form of an oscillating crystal. Battery connector 44a can be configured to be electrically connected to a power supply.

In one embodiment, test strip 24 can be in the form of an electrochemical glucose test strip. Test strip 24 can include one or more working electrodes and a counter electrode. Test strip 24 can also include a plurality of electrical contact pads, where each electrode is in electrical communication with at least one electrical contact pad. Strip port 22 can be configured to electrically interface to the electrical contact pads and form electrical communication with the electrodes of test strip 24. Test strip 24 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration value. The working electrode can then measure a concentration of the reduced mediator in the form of a current. In turn, DMU 10 can convert the current magnitude into a glucose concentration value.

Referring back to FIG. 1, insulin pen 28 can include a housing, preferably elongated and of sufficient size to be handled by a human hand comfortably. The device 28 is provided with electronic module 30 to record dosage amounts delivered by the user. The device 28 may include a second wireless module 32 disposed in the housing that, automatically without prompting from a user, transmits a signal to first wireless module 46 (See FIGS. 1 and 2) of the DMU 10. The wireless signal can include, in an exemplary embodiment, data to (a) type of therapeutic agent delivered; (b) amount of therapeutic agent delivered to the user; or (c) time or date of therapeutic agent delivered.

In one embodiment, a therapeutic delivery device can be in the form of a "user-activated" therapeutic delivery device, which requires a manual interaction between the device and a user (for example, by a user pushing a button on the device) to initiate a single therapeutic agent delivery event and that in the absence of such manual interaction deliver no therapeutic agent to the user. A non-limiting example of such a user-activated therapeutic agent delivery device is described in co-pending U.S. Provisional Application Nos. 61/040,024; 61/051,258; 61/082,106 and entitled Analyte Measurement and Management Device and Associated Methods, and 61/089,343, which is hereby incorporated in whole by reference. Another non-limiting example of such a user-activated therapeutic agent delivery device is an insulin pen 28. Insulin pens are loaded with a vial or cartridge of insulin, and are attached to a disposable needle. Portions of the insulin pen can be reusable, or the insulin pen can be completely disposable. Insulin pens are commercially available from companies such as Novo Nordisk, Aventis, and Eli Lilly, and can be used with a variety of insulin, such as Novolog, Humalog, Levemir, and Lantus. U.S. Patent Application Publication No. 2005/0182358 illustrates a drug delivery device for use in conjunction with a protocol from a health care provider. U.S. Patent Application Publication No. 2005/0182358 is hereby incorporated by reference into this application.

Referring to FIG. 1, a therapeutic dosing device can also be a pump 48 that includes a housing 50, a backlight button 52, an up button 54, a cartridge cap 56, a bolus button 58, a down button 60, a battery cap 62, an OK button 64, and a display 66. Pump 48 can be configured to dispense medication such as, for example, insulin for regulating glucose levels.

Figure 4:
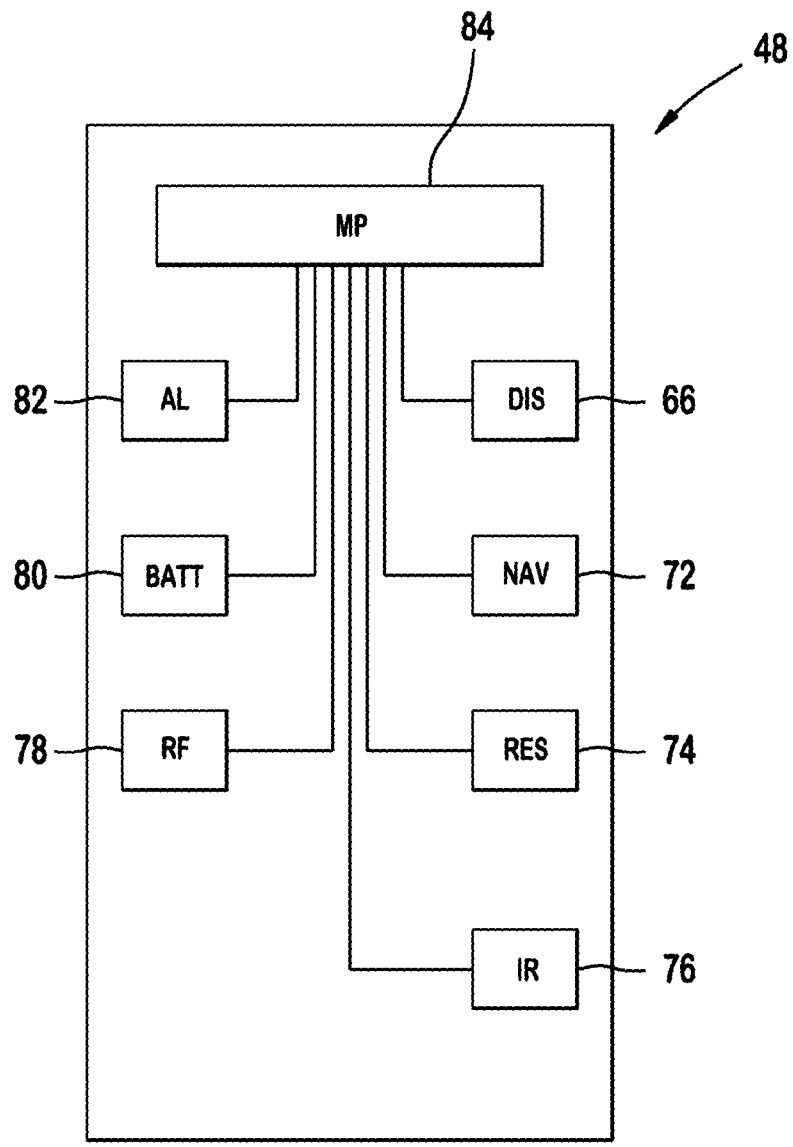
FIG. 4 illustrates a schematic of the functional components of an insulin pump, according to an exemplary embodiment described and illustrated herein.

Referring to FIG. 4, pump 48 includes the following functional components that are a display (DIS) 66, navigational buttons (NAV) 72, a reservoir (RES) 74, an infrared communication port (IR) 76, a radio frequency module (RF) 78, a battery (BAT) 80, an alarm module (AL) 82, and a microprocessor (MP) 84. Note that navigational buttons 72 can include up button 54, down button 60, and ok button 64.

Figure 5:
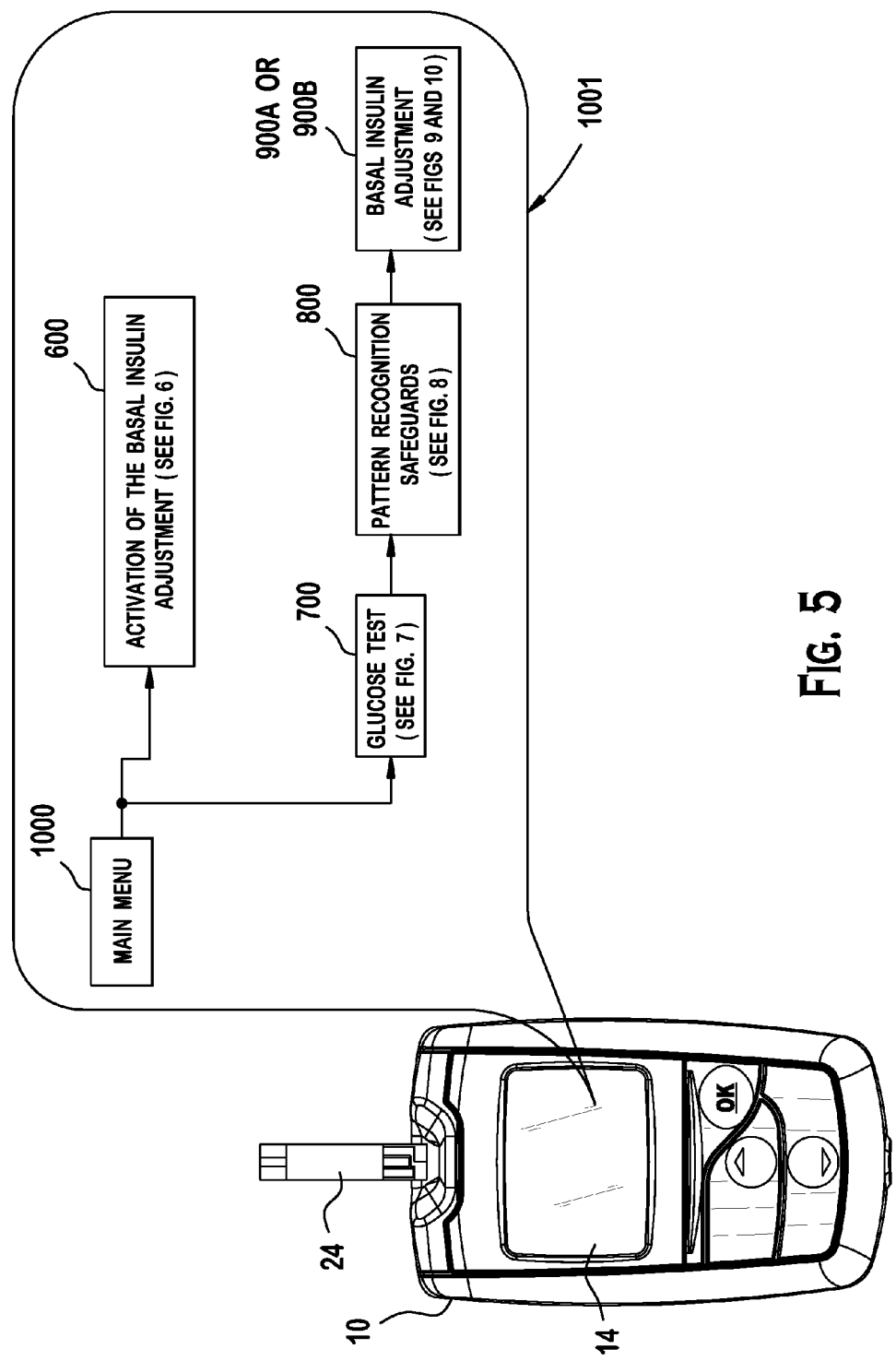
FIG. 5 illustrates a user interface of the analyte measurement and management device for providing basal insulin therapy, according to an exemplary embodiment described and illustrated herein.

FIG. 5 illustrates a user interface 1001 that provides basal insulin therapy in one of the DMUs, exemplarily shown here as a DMU 10. In one embodiment, programs and methods for conducting user interface 1001 can be stored on non-volatile memory 40 of DMU 10. Steps and instructions of user interface 1001 can be displayed on display 14 of DMU 10. Basal insulin therapy can calculate and/or adjust the amount of a recommended basal insulin dose. In another embodiment, a recommended basal insulin dose can be conveyed to an insulin pen either manually by the user or wirelessly from the DMU 10 to the pen 28.

In user interface 1001, a user can select a particular function or sub-routine such as activate basal insulin adjustment 600 (FIG. 6) or perform a glucose test 700 (FIG. 7), i.e., collecting data representative of a plurality of fasting blood glucose concentration values as measured by the test sensor of the handheld glucose-insulin data management unit. When performing glucose test 700, the following sub-routines can also be performed which include safeguards against hypoglycemia 800 (FIG. 8), which performs safeguards against hypoglycemia of the user prior to any change in basal insulin dose in adjustment 900 (FIG. 9) based on the plurality of data. Basal insulin adjustment 900 may be represented by either embodiment 900A or 900B (See FIGS. 9 and 10). Note if the basal insulin adjustment is not activated, then steps 800 and 900 cannot be performed. Activation of the basal insulin adjustment 600 allows a HCP, a diabetes educator, or a user to configure the setup settings and also allows the glucose meter to perform steps 800 and 900. Safeguards against hypoglycemia 800 can identify patterns such as a sufficiently low frequency of fasting glucose measurements, and a significant number of low glucose readings, either of which can cause a warning message to be outputted and/or a prohibition of the basal insulin adjustment 900. Thus, upon completion of the safeguard 800, a recommendation can be provided that may include one of no change in the current basal insulin dose, an increase or decrease in the current basal insulin dose as a function of at least three consecutive fasting glucose concentration values from the plurality of fasting blood glucose concentration values.

Applicants believe that the implementation of the method 900 on a glucose meter will simplify the process of adjusting basal insulin doses. However, applicant also believes that a HCP or diabetes educator should train the user beforehand so that the method can be properly set up on the meter. In one embodiment, the DMU will have method 900 on a memory portion of the meter that can be executed by a microprocessor. A HCP or diabetes educator can activate method 900 on the meter by inputting a special code to unlock this feature on the meter. Alternatively, a user may unlock the meter after being given the code from a HCP or diabetes educator. The following will describe a method 600 for activating the basal insulin adjustment.

Figure 6:
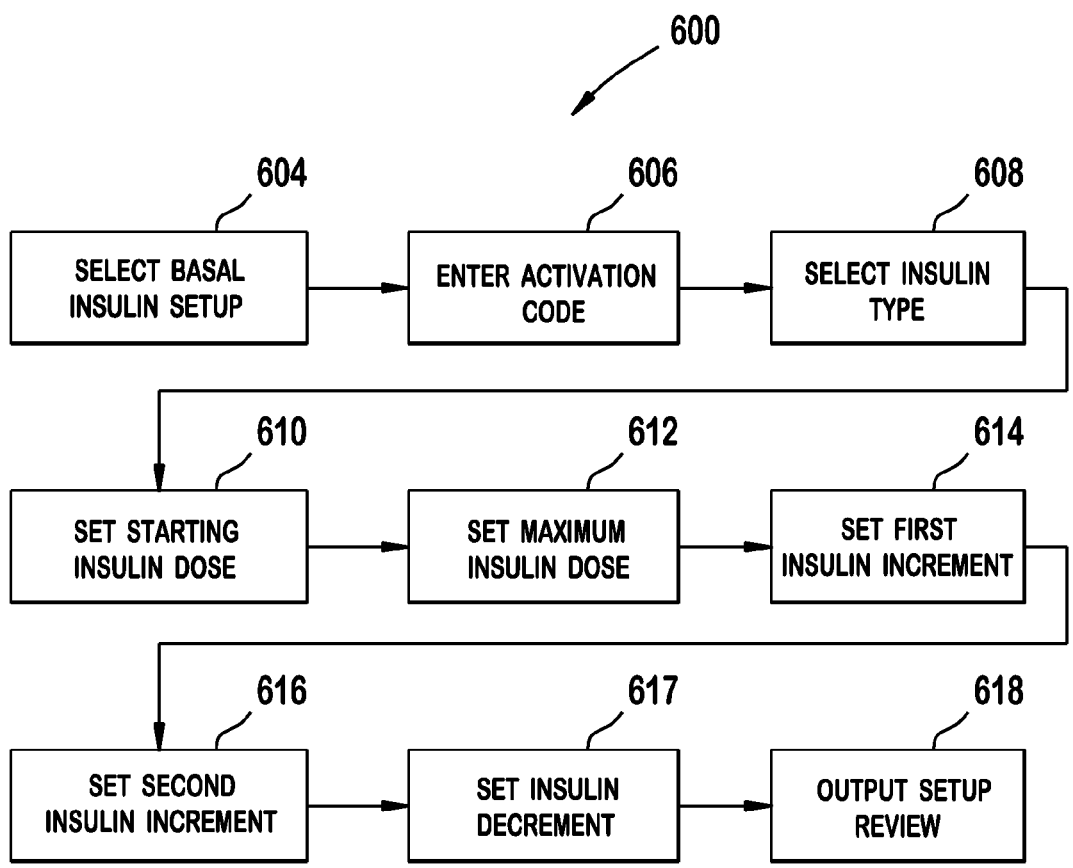
FIG. 6 is a flow chart illustrating an embodiment of a method for activating and setting up basal insulin therapy, according to an exemplary embodiment described and illustrated herein.

FIG. 6 is a flow chart illustrating an embodiment of a method 600 for activating and setting up a basal insulin adjustment. A user, HCP, or diabetes educator can select a basal insulin setup from a menu, as shown in step 604. If the basal insulin setup has not yet been activated, an activation code must be entered, as shown in step 606. In one embodiment, the activation code can be a four digit number that can be inputted into the meter when the user has been sufficiently trained. In one embodiment, the HCP or diabetes educator may activate the basal insulin adjustment by inputting the code into the DMU directly or through a personal computer connected to the DMU via the Internet. In another embodiment, the DMU may be activated by inserting a chip, dongle, electronic key, or non-electronic key. After entering the code, the following information can be inputted into the meter such as insulin type (step 608), starting insulin dose amount (step 610), maximum allowable insulin dose amount (step 612), a first and second insulin dose increment amount (step 614 and 616), and an insulin dose decrement (617). After the settings have been set, the settings can be outputted on the meter screen so that it can be reviewed for correctness, as shown in step 618.

The following provides details regarding the inputs for setting up the basal insulin adjustment. Referring to step 608, an insulin type may be Lantus, NPH, Detemir, or pre-mixed. Referring to step 610, a starting insulin dose may range from about 10 units to about 60 units. Referring to step 612, a maximum allowable insulin dose amount may range from about 50 units to about 100 units. Referring to steps 614 and 616, first insulin increment may range from about one to about four units and a second insulin increment may range from about two units to about eight units. Referring to step 616, a first insulin decrement may range from about zero to about ten units.

Figure 7:
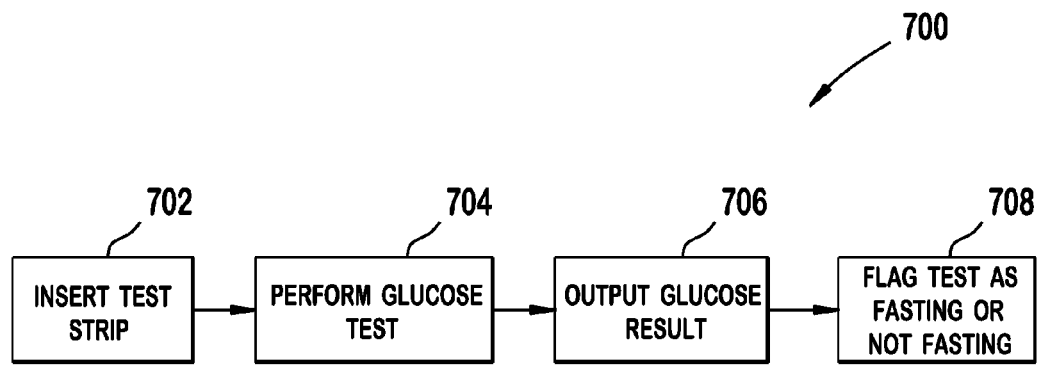
FIG. 7 is a flow chart illustrating an embodiment of a method for measuring glucose, according to an exemplary embodiment described and illustrated herein.

FIG. 7 is a flow chart illustrating an embodiment of a method 700 to measure blood glucose of a patient or user. A patient or user can initiate a glucose test by selecting a glucose test from main menu 1000 of by inserting a glucose test strip 24 into DMU 10, as shown in step 702. Next, the user can perform a glucose test by applying blood to the test strip, as shown in step 704. After a testing period, a glucose result can be displayed on the DMU, as shown in step 706. Next, the user can flag the test as conducted during a period in which user has not eaten in the last 6-8 hours, referred to here as "fasting" blood glucose, or conducted while not fasting, as shown in step 708. In the preferred method, a plurality of blood glucose concentration value of the user with the analyte test sensor over a plurality of time periods is measured and data representative of the plurality of fasting blood glucose concentration value with the handheld diabetes data management unit are collected. Next, safeguards against hypoglycemia 800 can be performed using data including the current glucose measurement and previous measurements.

Figure 8:
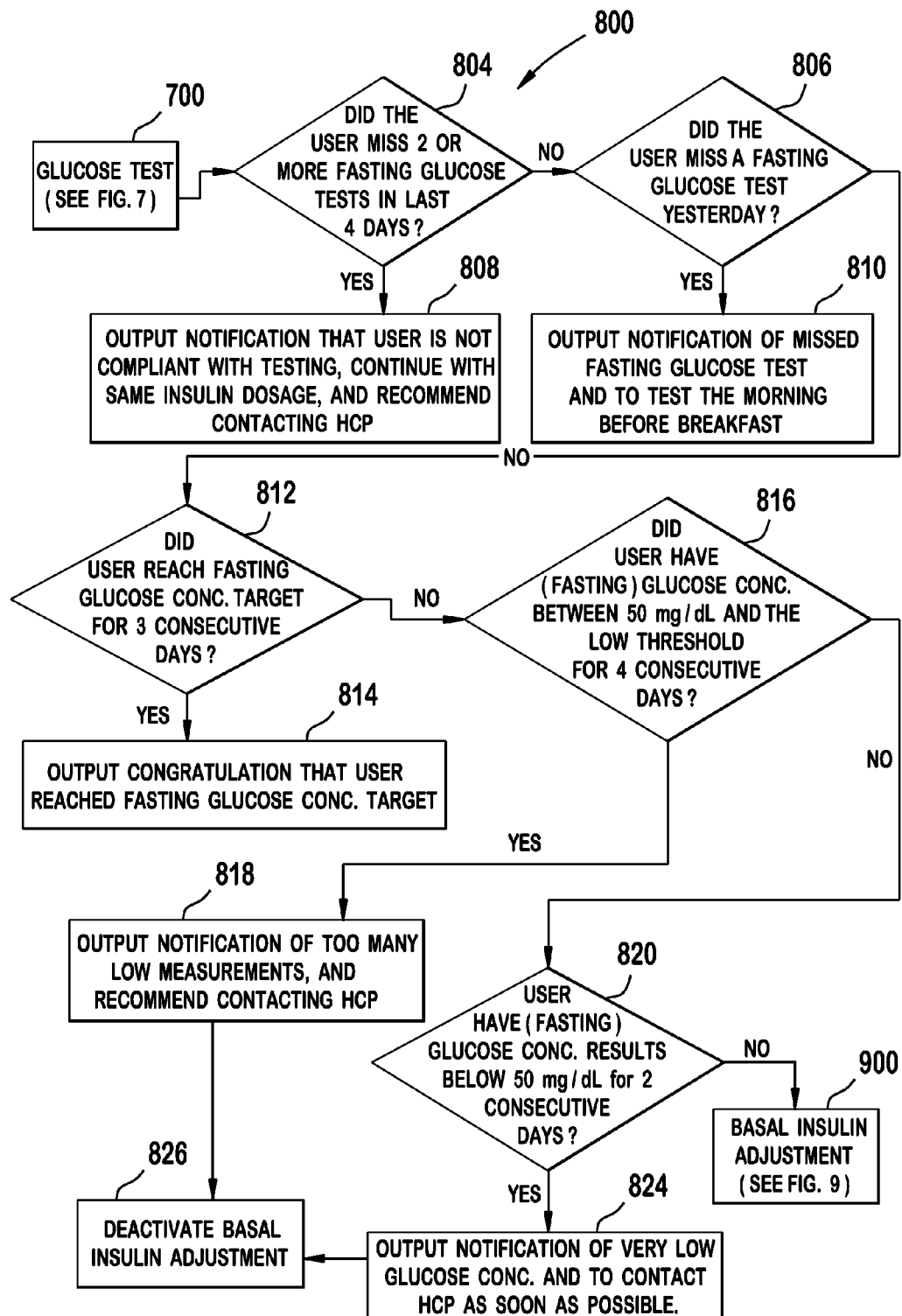
FIG. 8 is a flow chart illustrating an embodiment of a method for recognizing patterns and providing warning messages to a user who is on basal insulin therapy, according to an exemplary embodiment described and illustrated herein.
Figure 9:
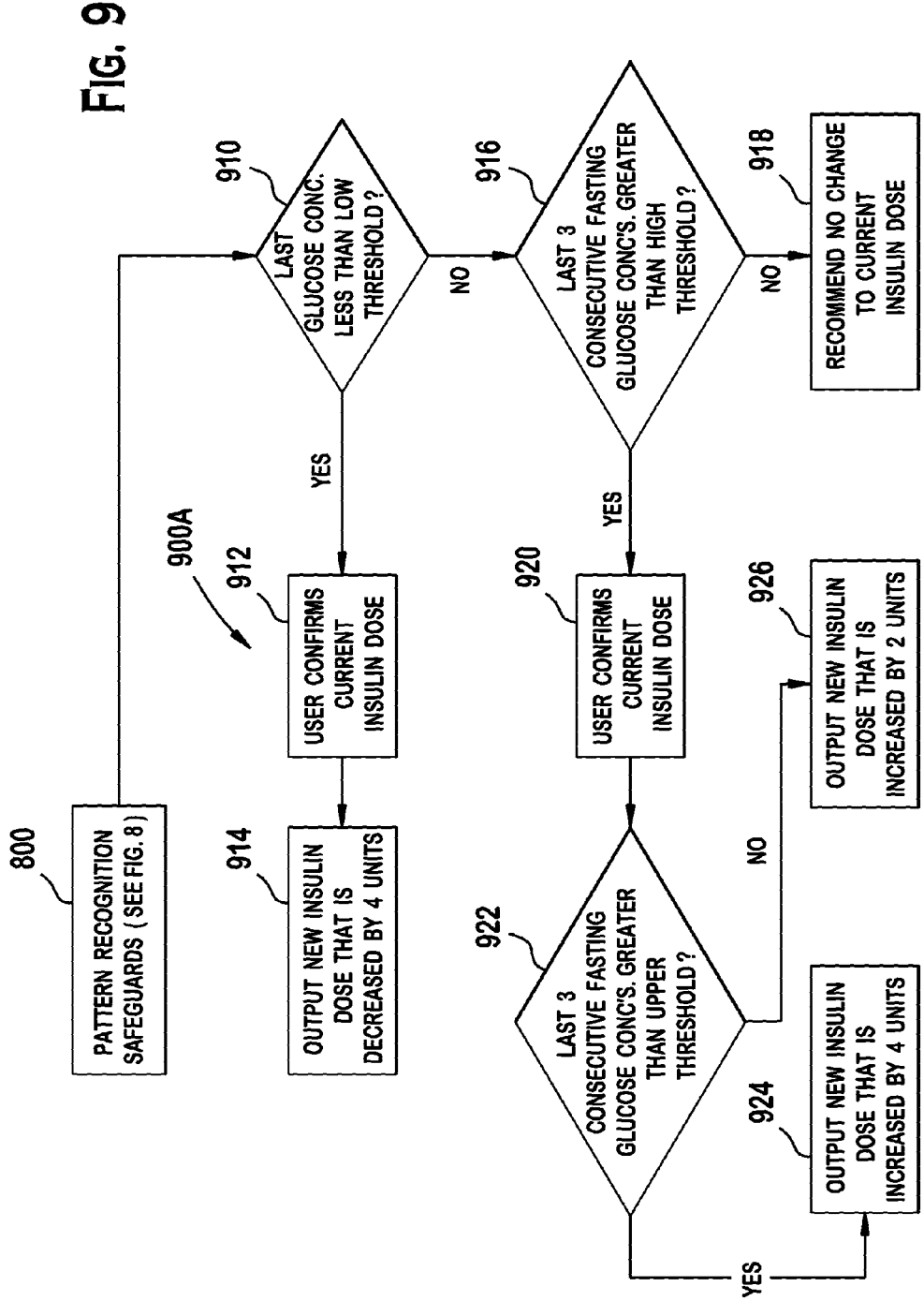
FIG. 9 is a flow chart illustrating an embodiment of a method for increasing or decreasing an amount of insulin for basal therapy, according to an exemplary embodiment described and illustrated herein.

Applicant believes that safeguards should be implemented for the process of adjusting a user's basal insulin dose to guard against hypoglycemia of the user. As shown in FIG. 8, a method 800 can be used to recognize particular patterns that cause a user to not receive a recommended basal dosage amount of insulin (i.e., deactivation or prohibition). If a user misses a sufficient number of fasting glucose test or has a sufficient number of low glucose concentration values, then the meter may not output a recommended basal insulin dose and may optionally deactivate or prohibit basal insulin adjustment 900 (FIG. 9). Note that a user can miss a sufficient number of fasting glucose tests by either not testing or by not flagging the glucose measurement as fasting. Hence, from the collected data it is ascertained as to whether the user has conducted a minimum number fasting blood glucose concentration measurements within at least one of four prescribed time periods.

Referring again to FIG. 8, the data management unit can determine whether the collected data indicate one of a first low blood glucose concentration pattern (step 818) and a second low blood glucose concentration pattern (step 824) lower than the first low blood glucose concentration pattern. In particular, after a glucose test is performed, the meter can perform a series of queries such as whether a user missed two or more fasting glucose tests in the last four days (step 804), whether a fasting glucose test was missed yesterday (step 806), whether the fasting glucose concentration values were within target for three consecutive days (step 812), whether the fasting glucose concentration value was between a first low value and the low threshold for four consecutive days (step 816), and whether the fasting glucose concentration value results were below the first low value for two consecutive days (step 820).

Note that the first low value can be a glucose concentration of about 50 mg/dL or less. Although steps 816 and 820 refer to a fasting glucose concentration, in one embodiment, method 800 can use any glucose concentration (i.e., fasting and non-fasting) such as, for example, glucose concentrations measured pre-meal, post-meal, before bedtime, before or after breakfast, before or after lunch, before or after dinner, and before or after exercise.

Referring back to steps 816 and 820, consecutive days can include a first day having a first glucose measurement and a second day having a second glucose measurement where the first and second glucose measurements were measured such that two measurements are apart by at least more than a first time interval. In an embodiment, the first time interval is greater than about two hours. By requiring a minimum amount of time between the glucose concentration measurements, pattern recognition safeguards 800 will not prematurely deactivate the insulin algorithm. For example, if two glucose measurements were performed on 11:45 pm on day one and at 12:01 am (six minutes later) on the following day, method 800 would not characterize those two glucose measurements as being on consecutive days.

Note that the meter preferably saves date, time, and flag type with each glucose measurement to a memory portion, which allows a microprocessor to perform the above queries (804, 806, 812, 816, and 820). That is, upon determination of at least one of the first and second low blood glucose concentration patterns (step 818 or 824) of the user, safety notifications are displayed on the display screen of the handheld diabetes data management unit. In particular, if the queries (804, 806, 812, 816, and 820) are all negative, then the DMU 10 can output a suggested basal insulin dose using basal insulin adjustment 900. However, if one of the queries (804, 806, 812, 816, and 820) is in the affirmative, then the DMU 10 may output a notification and may recommend that the user contact a HCP or diabetes educator. In another embodiment, the DMU 10 may output a warning, deactivate or prohibit basal insulin adjustment 900 if the maximum insulin dose is used, the frequency of insulin adjustments is too high, or the glucose concentration values are sufficiently hypoglycemic for a period of time.

The following will describe the messages provided to the user when one of the queries (804, 806, 812, 816, and 820) is in the affirmative. If two or more fasting glucose tests in the last four days were missed (804), then the DMU 10 can output a notice of non-compliance in testing and recommend contacting a HCP, as shown in step 808. Note that query 804 can be modified by a HCP or user to change the number of fasting glucose measurements required and the number of days used for the query. If a fasting glucose test was missed yesterday (806), then the DMU 10 can output a notification of a missed fasting glucose test and recommend that the user test in the morning before breakfast, as shown in step 810. If the fasting glucose concentration values were within target for three consecutive days (12), then the DMU 10 can output a congratulatory message that the user reached the fasting glucose concentration value target, as shown in step 814. If the fasting glucose concentration value was between 50 mg/dL and the low threshold for four consecutive days (816), then the DMU 10 can output a notification of too many low measurements and recommend that the user contact a HCP, as shown in step 818. If the fasting glucose concentration value results were below 50 mg/dL for two consecutive days (820), then the DMU 10 can output a notification of very low glucose concentration values and recommend that the user contact a HCP as soon as possible, as shown in step 824. Optionally, basal insulin adjustment 900 can be deactivated in step 826 after either the occurrence of step 818 or 824.

FIG. 9 is a flow chart illustrating an embodiment of a first method 900A for increasing or decreasing an amount of insulin for basal therapy. In one embodiment, a user can initially be prescribed a relatively low basal insulin dose of about 10 units, which should be taken every evening or before going to bed. Typically, a user will have to uptitrate to about 40 units to about 55 units to receive the benefit of basal insulin therapy where the fasting glucose levels are essentially in the euglycemic zone and the HbA1c levels are also in a targeted zone.

Once safeguards against hypoglycemia 800 have been performed, the DMU 10 can then determine whether the glucose concentration value is below a low threshold, as shown in step 910. The low threshold may range from about 60 mg/dL to about 100 mg/dL, or preferably be about 70 mg/dL. Note also that step 910 can be modified by a HCP or a user to require that, instead of only one glucose measurement, two to three consecutive glucose measurements must be less than the low threshold. If the fasting glucose concentration value is less than the low threshold, the DMU 10 can output the current basal insulin dose on a display of the DMU 10, as shown in step 912. Once the user confirms the current basal insulin dose, the DMU 10 can decrease the insulin dose by a first decrement, such as, for example, about four units, as shown in step 914.

If the glucose concentration value is not below a low threshold, then the DMU 10 will determine whether the last three fasting glucose measurements were greater than a high threshold, as shown in step 916. In one embodiment, a summary screen may be displayed immediately before or after step 916 where the last three fasting glucose measurement values are displayed on display 14 and the lowest value is highlighted. The high threshold may range from about 100 mg/dL to about 140 mg/dL, or preferably be about 130 mg/dL. If the fasting glucose concentration value is less than the high threshold, then no recommendation to change the current insulin dose will be made, as shown in step 918. If the glucose concentration value is greater than the high threshold, the DMU 10 can output the current basal insulin dose on a display of the DMU 10, as shown in step 920. Once the user confirms the current basal insulin dose, the DMU 10 can determine whether the last three fasting glucose measurements were greater than an upper threshold, as shown in step 922. The upper threshold may range from about 160 mg/dL to about 200 mg/dL, or preferably be about 180 mg/dL. Note that the upper threshold is greater than the high threshold. Note also that steps 916 and 922 can be modified by a HCP or a user to require that a different frequency of consecutive fasting glucose measurements be within a certain range over a different period of days. The DMU 10 can recommend a new insulin dose that is increased by a first increment (e.g., about about two units) where the last 3 consecutive fasting glucose concentration values are less than the upper threshold, but greater than the high threshold, as shown in step 924. Alternatively, the DMU 10 can recommend a new insulin dose that is increased by a second increment (e.g., about four units) where the last three consecutive fasting glucose concentration values are greater than the upper threshold, as shown in step 326. In one embodiment, a basal insulin dose can be taken in the evening before going to bed.

Figure 10:
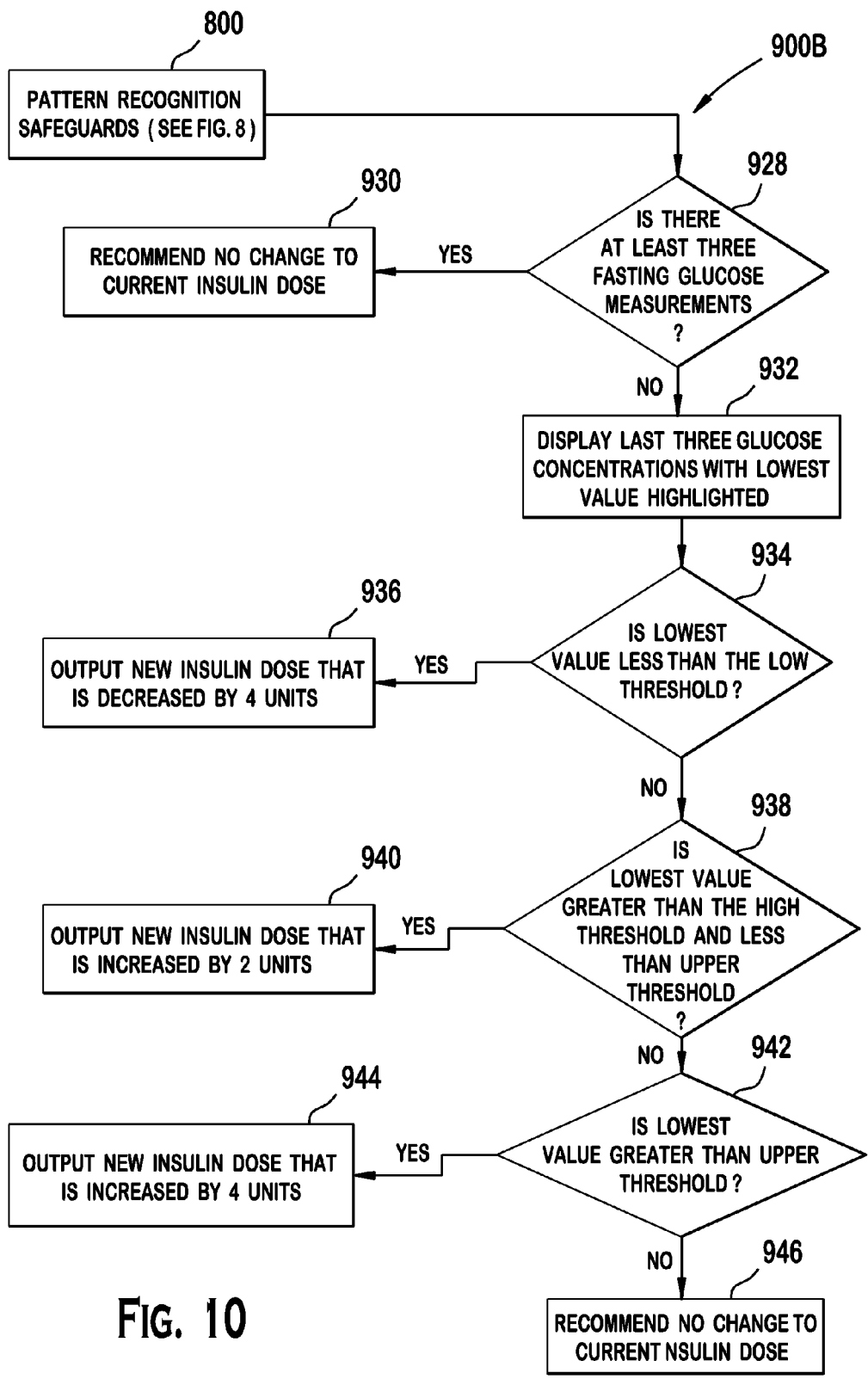
FIG. 10 illustrates flow chart illustrating another embodiment of a method for increasing or decreasing an amount of insulin for basal therapy, according to an exemplary embodiment described and illustrated herein.
Figure 11:
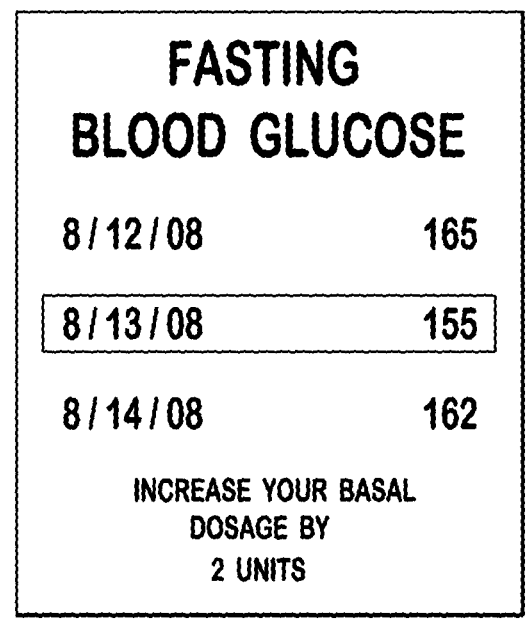
FIG. 11 illustrates screen shot of the user interface for the method of FIG. 10, according to an exemplary embodiment described and illustrated herein.

FIG. 10 is a flow chart illustrating another embodiment of a second method 900B for increasing or decreasing an amount of insulin for basal therapy, which method 900B can be used in place of method 900A or in conjunction thereto. As was before, once safeguards against hypoglycemia 800 have been performed, the DMU 10 can then determine whether there are at least three fasting glucose measurements in memory 40, as shown in step 928. If there are at least three fasting glucose concentration values, the DMU 10 can output a recommendation to not change the current insulin dose, as shown in step 930. However, if there are at least three fasting three fasting glucose concentration values, then the DMU 10 can display the last three fasting glucose concentration values on display 14 where a lowest glucose concentration value of the three is highlighted, as shown in step 932 and a screenshot of FIG. 11.

The DMU 10 can then determine whether the lowest value of the three glucose concentration values is below a low threshold, as shown in step 934. If the lowest fasting glucose concentration value is less than the low threshold, the DMU 10 can output a decrease of the insulin dose by a first decrement, such as, for example, about four units, as shown in step 936. However, if the lowest value is not below a low threshold, then the DMU 10 will determine whether the lowest value is greater than the high threshold and less than the upper threshold, as shown in step 938.

The DMU 10 can recommend a new insulin dose that is increased by a first increment (e.g., about two units) where the lowest value is greater than the high threshold, but less than the upper threshold, as shown in step 940. Alternatively, the DMU 10 can determine whether the lowest value is greater than the upper threshold, as shown in step 942. If the lowest value is greater than the upper threshold, then the DMU 10 can recommend a new insulin dose that is increased by a second increment (e.g., about four units), as shown in step 944. If the lowest value is not greater than the upper threshold, then the DMU 10 can recommend no change to the current insulin dose, as shown in step 946.

In one embodiment, method 1001 can be used to output a recommended basal insulin dose that is adjusted based on previous fasting glucose measurements. The recommended dose information can be transferred from first wireless transceiver 46 of DMU 10 to second wireless transceiver of insulin pen 28. A dosage selector of insulin pen 28 can be automatically adjusted to the recommended dose so that a user merely has to press a button on insulin pen 28 to input the recommended amount. When the user presses the button on insulin pen 28, this can cause a signal to be transmitted to DMU 10 so that the time, date, and dosage amount can be recorded to a memory portion of the DMU.

Referring to FIG. 1, personal computer 26 can be used to communicate with DMU 10 and insulin pen 28. In one example, computer 26 can also be connected via a mobile network to device 10 or 28. Alternatively, the computer 26 can be connected for communication via a short-range wireless network such as, for example, infrared, Bluetooth or WiFi. In the system shown exemplarily, computer 26 can be located remotely in a diabetes clinic or hospital so that certain therapeutic protocols, which have been customized for a particular diabetic user's physiological requirements, can be transferred to such a user remotely. For example, setting up of basal insulin therapy on DMU 10 can be performed remotely using computer 26. More specifically, steps in FIG. 3 such as selecting insulin type 208, starting insulin dose 210, maximum insulin dose 212, insulin dose increment and decrement can be set remotely using computer 26. Connecting analyte measurement device 10 with a local or remote computer can facilitate improved treatment by health care providers.

In order for the basal insulin therapy of method 1001 to be effective, the user should have a relatively high compliance in performing fasting glucose measurements and also in flagging such measurements as fasting. Accordingly, a predictive process can be implemented on DMU 10 to increase user compliance in flagging fasting glucose measurement as fasting. The following will describe a predictive process that can be implemented for recommending a type of flag before or after outputting a glucose result in step 706 of FIG. 7. Once a fasting flag is recommended, the user will have the option of accepting the recommended flag or rejecting it. Applicants believe that by recommending a correct flag at a high percentage of the time will cause users to flag measurements with a higher degree of compliance because only one button needs to be pressed to accept the recommendation.

In one embodiment, a fasting flag can be recommended based on the time, the day, and/or past user testing patterns. For example, if a user had selected the "fasting" flag at 7 am multiple times, then the meter will suggest that the same "fasting" flag for the next reading performed at around 7 am. In one embodiment, the predictive process may require that at least "n" glucose readings be performed during the same time period with a fasting flag. The minimum number of glucose readings having a matching flag during a particular time interval can be adjusted by the user or health care provider. For example, the sub-routine can require that three of the last five glucose readings for a particular time period have the fasting flag. A time period can be defined as a two hour period, but optionally can be adjusted by the user or health care provider. Once a user is presented with a recommended fasting flag, the user has the option to override the suggestion or accept it.

In another embodiment, a fasting flag can be recommended if the test is the first test of the day. A microprocessor and clock of the DMU 10 can determine the first time in which it is turned on. In another embodiment, a fasting flag can be recommended based on a user inputted meal time schedule. Before performing a glucose test, the user may use the user interface of DMU 10 to input the meal time schedule. Alternatively, a default meal time schedule can be saved to a memory portion of the meter at the factory. If the glucose test is performed before a first meal of the day, then the fasting flag can be recommended. In another embodiment, a fasting flag can be recommended if the glucose test is the first test of the day and is in the morning such as, for example, between 6 am to 10 am. A morning time interval can be defined by the user or be a default setting set when the meter is manufactured.

As noted earlier, the microprocessor can be programmed to generally carry out the steps of various processes described herein. The microprocessor can be part of a particular device, such as, for example, a glucose meter, an insulin pen, an insulin pump, a server, a mobile phone, personal computer, or mobile hand held device. Furthermore, the various methods described herein can be used to generate software codes using off-the-shelf software development tools such as, for example, C, C+, C++, C-Sharp, Visual Studio 6.0, Windows 2000 Server, and SQL Server 2000. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microprocessor or computer, are operable to carry out the steps described in these methods along with any other necessary steps.

While preferred embodiments of the present invention have been shown and described herein, it will be obvious to those skilled in the art that such embodiments are provided by way of example only. For example, the invention can be applied not only to docking stations and glucose meters, but can also be applied to any electronic device that needs a power supply and that can be re-set such as insulin infusion pump, continuous glucose monitoring system and the like. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. A method for management of diabetes for basal insulin dosing of a user with an insulin delivery device and a handheld diabetes data management unit having an analyte test sensor, a processor coupled to a memory and display screen, the method comprising:
   measuring a plurality of blood glucose concentration values of the user with the analyte test sensor over a plurality of time periods;
   collecting data representative of a plurality of fasting blood glucose concentration values with the handheld diabetes data management unit;
   ascertaining from the collected data whether the user has conducted a minimum number of fasting blood glucose concentration measurements within at least one of four prescribed time periods;
   determining whether the collected data indicate one of a first low blood glucose concentration pattern and a second low blood glucose concentration pattern lower than the first low blood glucose concentration pattern;
   evaluating whether basal insulin adjustment in the handheld diabetes data management unit is appropriate in the event that glucose concentration value results for two consecutive days are below a first low value for a first pattern;
   evaluating whether basal insulin adjustment in the handheld diabetes data management unit is appropriate in the event that glucose concentration value results for four consecutive days are each between about a low threshold and about a first low value for a second pattern;
   upon determination of at least one of the first and second low blood glucose concentration patterns of the user, displaying safety notifications on the display screen of the handheld diabetes data management unit; and
   prohibiting basal insulin adjustment in one of the insulin delivery device and handheld diabetes data management unit whenever either one of the first or second low blood glucose concentration pattern is determined.

2. The method of claim 1, in which consecutive days include a first day having a first glucose measurement and a second day having a second glucose measurement, where the two glucose measurements are apart by at least more than a first time interval.

3. The method of claim 2, in which the first time interval is greater than about two hours.

4. The method of claim 2, in which the determining comprises recommending insulin dosage that is decreased by a first decrement where a prior last glucose concentration value is less than a first low threshold.

5. The method of claim 2, in which the determining comprises recommending no changes to a current insulin dose stored in the memory of the handheld diabetes data management unit in the event that all three prior consecutive fasting blood glucose concentration values are not higher than a high threshold; and recommending, in the event that all three prior consecutive fasting blood glucose concentration values are greater than an upper threshold, an increase in insulin by a first increment, otherwise recommending an increase in insulin by a second increment.

6. The method of claim 2, in which the evaluating comprises determining whether there are at least three fasting blood glucose measurements stored in the handheld diabetes data management unit and if true, recommending no changes to current insulin dose otherwise displaying last three blood glucose concentration values with a lowest of the three values highlighted.

7. The method of claim 6, in which the determining comprises deciding whether the lowest value is less than a predetermined low threshold and if true then displaying a new insulin dose having a value less than a current insulin dose stored in the memory of the handheld diabetes data management unit by a decreased value.

8. The method of claim 7, in which the decreased value comprises about 4 units.

9. The method of claim 6, in which the determining comprises deciding whether the lowest value is greater than a predetermined high threshold and less than a predetermined upper threshold and if true displaying a new insulin dose having an increased value greater than a current insulin dose stored in the memory of the handheld diabetes data management unit.

10. The method of claim 9, in which the increased value comprises about 2 units.

11. The method of claim 6 in which the determining comprises deciding whether the lowest value is greater than a predetermined upper threshold value and if true, displaying a new insulin dose having an increased value greater than a current insulin dose stored in the memory of the handheld diabetes data management unit.

12. The method of claim 11, in which the increased value comprises about 4 units.

13. The method of claim 1, in which the glucose concentration value results comprise fasting glucose value results.

14. The method of claim 1, in which the ascertaining comprises determining whether the fasting blood glucose concentration values of the user are within predetermined target for a predetermined period of time.

15. The method of claim 14, in which the predetermined period comprises approximately three consecutive days.

16. The method of claim 1, in which the ascertaining comprises determining whether the user has missed at least two fasting blood glucose tests in the first time period.

17. The method of claim 16, in which the determining comprises notifying the user, in the event that the user: (a) has missed at least two fasting blood glucose tests during the first time period, (b) is not compliant with testing, or (c) is to continue with prescribed insulin dosage; and recommending that the user contacts a health care provider.

18. The method of claim 1, in which the ascertaining comprises determining whether the user has missed a one day prior fasting glucose test.

19. The method of claim 1, further comprising
flagging a recent glucose concentration value as a fasting measurement;
displaying a recommended insulin dosage that is increased by a first increment where the last three glucose concentration value are all greater than a high threshold but less than an upper threshold;
displaying a recommended insulin dosage that is increased by a second increment where the last three glucose concentration value are all greater than an upper threshold;
deactivating the basal adjustment algorithm where the user misses two or more fasting glucose measurements over a four day period;
providing a warning message where the user misses a fasting glucose measurement yesterday; or
deactivating the basal adjustment algorithm where four consecutive fasting glucose concentration values are less than 50 mg/dL.

20. A method to safeguard basal insulin dose changes with an insulin delivery device and a handheld diabetes data management unit having a test sensor, a processor coupled to a memory and display, the method comprising:
collecting data representative of a plurality of fasting blood glucose concentration values as measured by the test sensor of the handheld diabetes data management unit;
performing safeguards against hypoglycemia of the user prior to any change in basal insulin dosage based on the plurality of data, wherein the safeguards comprise:
prohibiting basal insulin adjustment in one of the insulin delivery device and handheld diabetes data management unit ascertaining from the collected data whether the user has conducted a minimum number fasting blood glucose measurements within at least one of two prescribed time periods;
determining whether the collected data indicates one of a first low blood glucose concentration pattern and a second low blood glucose concentration pattern; and
upon determination of at least one of the first and second low blood glucose concentration patterns of the user, displaying respective safety notifications on the display screen of the handheld diabetes data management unit; and
upon completion of the safeguards, recommending one of no change in the current basal insulin dose, an increase or decrease in the current basal insulin dose as a function of at least three consecutive fasting glucose concentration values from the plurality of fasting blood glucose concentration values.

21. The method of claim 20, in which the determining comprises recommending insulin dosage that is decreased by a first decrement where a prior last glucose concentration value is less than a first low threshold;
recommending no changes to a current insulin dose stored in the memory of the handheld diabetes data management unit in the event that all three prior consecutive fasting blood glucose concentration values are not higher than a high threshold; and
in the event that all three prior consecutive fasting blood glucose concentration values are greater than a upper threshold, recommending an increase in insulin by a first increment otherwise recommending an increase in insulin by a second increment.

22. The method of claim 20, in which the recommending comprises determining whether there are at least three fasting blood glucose measurements stored in the handheld diabetes data management unit and if true, recommending no changes to current insulin dose otherwise displaying last three blood glucose concentration values with a lowest of the three values highlighted; and deciding whether the lowest value is less than a predetermined low threshold and if true then displaying a new insulin dose having a value less than a current insulin dose stored in the memory of the handheld diabetes data management unit by a decreased value.

23. The method of claim 22, in which the decreased value comprises about 4 units.

24. The method of claim 20, in which the recommending comprises deciding whether the lowest value is greater than a predetermined low threshold and less than a predetermined upper threshold and if true displaying a new insulin dose having an increased value greater than a current insulin dose stored in the memory of the handheld diabetes data management unit.

25. The method of claim 24, in which the increased value comprises about 2 units.

26. The method of claim 20, in which the recommending comprises deciding whether the lowest value is greater than a predetermined upper threshold value and if true, displaying a new insulin dose having an increased value greater than a current insulin dose stored in the memory of the handheld diabetes data management unit.

27. The method of claim 26, in which the increased value comprises about 4 units.

* * * * *